United States Patent
Kishimoto et al.

(10) Patent No.: US 7,459,482 B2
(45) Date of Patent: Dec. 2, 2008

(54) AGENT FOR TREATMENT OF CISPLATIN-RESISTANT CANCER

(75) Inventors: Shuichi Kishimoto, Kobe (JP); Shoji Fukushima, Kobe (JP); Yoshikazu Takeuchi, Akashi (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 11/495,709

(22) Filed: Jul. 31, 2006

(65) Prior Publication Data

US 2006/0264502 A1    Nov. 23, 2006

Related U.S. Application Data

(62) Division of application No. 10/344,239, filed as application No. PCT/JP01/06798 on Aug. 8, 2001.

(30) Foreign Application Priority Data

Aug. 11, 2000   (JP)   ............... 2000-244463

(51) Int. Cl.
*A61K 31/282* (2006.01)

(52) U.S. Cl. ........................ 514/492; 424/776

(58) Field of Classification Search ................ 514/492; 424/776
See application file for complete search history.

(56) References Cited

U.S. PATENT DOCUMENTS 4,562,275 A * 12/1985 Speer et al. .................. 556/7
5,384,127 A    1/1995 Perez-Soler et al.
6,613,799 B1   9/2003 Maeda et al.

FOREIGN PATENT DOCUMENTS

EP    193936 A1    9/1986

OTHER PUBLICATIONS

Fujiyama et al. (British J. of Cancer (2003) 89, 1614-1619.*
www.stJude.org/solid-tumor 2-pages (Apr. 2003).*
Kishimoto et al., Biol. Pharm Bull. Apr. 2000;23(3):344-8.*
Kishimoto et al., Biol. Pharm Bull. Apr. 2000;23(4):487-91.*
Kishimoto et al., Jpn. J. Cancer Res. 91, 1326-1332, Dec. 2000.*
Kishimoto, S., et al., Jpn. J. Cancer Res., vol. 91, No. 12, pp. 1326-1332, Dec. 2000.
Kishimoto, S., et al., Jpn. J. Cancer Res., vol. 91, No. 1, pp. 99-104, Jan. 2000.
Miyazawa, K. et al., Drug Delivery Syst., vol. 14, No. 5, pp. 401-405, 1999.
Jpn. J. Cancer Chemother., vol. 10, pp. 2442-2452, (1983), (English abstract).
Goddard et al., Ann. Of Onocoloty, vol. 2, pp. 535-540, (1991).
Twentyman et al., Cancer Research, vol. 52, pp. 5674-5680, (1992).
Han et al., Cancer Research, vol. 53, pp. 4913-4919, (1993).
Biochemical Pharmacology, vol. 30, No. 19, pp. 2721-2723, (1981).
Eichholz-Wirth et al., Br. J. Cancer, vol. 54, pp. 239-243. (1986).
Metcalfe et al., Cancer Letters, vol. 31, pp. 163-169, (1986).
Rixe et al., Bio. Pharm., vol. 52, pp. 1855-1865, (1996).
Perez-Soler et a., Cancer Research, vol. 48, pp. 4509-4512, (1988).
Drug Delivery Systems, vol. 5, pp. 243-247, (1990), (English abstract).
J. Jpn. Soc. Cancer Ther., vol. 27, pp. 49-58, (1992), (English abstract).
Kishimoto et al., Reg. Cancer Treat., vol. 1-2, pp. 25-29, (1992).
Kishimoto et al., Biol. Pharm. Bull., vol. 23, No. 3, pp. 334-348, (2000).
Kishimoto et al., Biol. Pharm. Bull., vol. 23, No. 4, pp. 487-491, (2000).
Heike et al., Cancer Chemother. Pharmacol., vol. 35, pp. 200-204, (1995).

* cited by examiner

*Primary Examiner*—Michael G. Hartley
*Assistant Examiner*—Shirley V Gembeh
(74) *Attorney, Agent, or Firm*—Birch, Stewart, Kolasch & Birch, LLP

(57) ABSTRACT

Preparation of a lipophilic platinum complex being dissolved or suspended in an iodized poppyseed oil fatty acid ethyl ester is useful as an agent for treatment of cisplatin-resistant cancers.

4 Claims, 2 Drawing Sheets

AGENT FOR TREATMENT OF CISPLATIN-RESISTANT CANCER

This application is a divisional application of application Ser. No. 10/344,239, filed on Feb. 11, 2003, which is the national phase under 35 U.S.C. § 371 of PCT International Application No. PCT/JP01/06798 which has an International filing date of Aug. 8, 2001, which designated the United States of America. The entire contents of the above-identified application are hereby incorporated by reference, and priority is claimed under 35 U.S.C. § 120.

TECHNICAL FIELD

The present invention relates to a method for promoting the uptake of a platinum complex into cancer cells, which comprises administering a solution or suspension of a lipophilic platinum complex in an iodized poppyseed oil fatty acid ethyl ester, and further relates to an agent for treatment of cisplatin-resistant cancer which comprises as an active ingredient a lipophilic platinum complex being dissolved or suspended in an iodized poppyseed oil fatty acid ethyl ester.

BACKGROUND ART

Cisplatin (CDDP) is a platinum complex having a wide anticancer spectrum and potent anti-tumor activity, and has contributed to the improvement of treatment results of various cancers as a key medicament in combination of multiple drugs for the treatment of solid cancers. However, cisplatin shows serious side effects such as serious nephrotoxic, nausea and vomiting, and further the existence of cancers being resistant against cisplatin becomes clinical problems for the treatment of cancers. Under these circumstances, it has been reported that a number of platinum complexes having 1,2-diaminocyclohexane (DACH) and 1,2-diaminocycloheptane as ligands do not show cross-resistance to cisplatin-resistant L1210 murine leukemia cells, and maintain their anti-tumor activity (cf. Jpn. J. Cancer Chemother., 10, pp 2442-2451 (1983)). However, in the research thereafter, there are cases wherein certain cisplatin resistant cancer cells shows sensitivity to platinum complexes having DACH ligand, but other cisplatin-resistant cancer cells show cross-resistance to the said platinum complexes having DACH ligand, or cases wherein certain cisplatin resistant cancer cells show sensitivity to certain platinum complexes but show cross-resistance to other platinum complexes (cf. Ann. Oncol., 2, 535-540 (1991); Cancer Research, 52, 5674-5680 (1992); ibid., 53, 4913-4919 (1993), etc.). The reasons therefor have been studied, and speculated to be due to the properties of each cell or the resistance mechanism thereof, but they have not been clarified yet.

The mechanism of having resistance of cancer cells to platinum complexes such as cisplatin may be, for example, decrease in the uptake of platinum into cells, increase in glutathione and metallothionein level as intracellular detoxication, increase of DNA repair ability, increase of permissibility to DNA injury, etc. (cf., Biochem. Pharmacol., 30, 2721-2723 (1981); Br. J. Cancer, 54, 239-243 (1986); Cancer Lett., 31, 163-169 (1986); Biochem. Pharmacol., 52, 1855-1865 (1996)).

It has been reported that a liposome preparation containing cis-bis(neodecanoato)-(1R,2R)-1,2-diamino-cyclohexane platinum (II) are more effective to cisplatin-resistant cancers (cf., Cancer Research, 48, 4509-4512 (1988); ibid., 53, 4913-4919 (1993)).

It has been reported that a preparation (SM-11355/LPD), which is prepared by suspending the following cis[((1R,2R)-1,2-cyclohexanediamine-N,N')bis(myristato)]platinum (II) (abbreviated as SM-11355) in an iodized poppyseed oil fatty acid ethyl ester (Lipiodol™: abbreviated as LPD), showed potent anti-tumor effects in a rat hepatic cancer model and rabbit VX-2 transplantable hepatic cancer model by administering to the hepatic artery, where the platinum complex is retained in the hepatic cancer tissues for a prolonged period and thereby is gradually released (cf., Ono et al., J. Jpn. Soc. Cancer Ther., 27, 49-58 (1992); Kishimoto et al., Drug Delivery Systems, 5, 243-247 (1990); Kishimoto et al,. Reg. Cancer Treat., 1-2, 25-29 (1992)); Kishimoto et al., Biol. Pharm. Bull., 23, 344-348 (2000)).

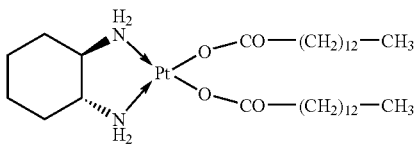

DISCLOSURE OF INVENTION

An object of the present invention is to provide a method for promoting the uptake of a platinum complex into cancer cells, and further to provide a pharmaceutical preparation for treating cisplatin-resistant cancer by using the same. The present inventors have found that the uptake of a platinum complex into cancer cells is promoted by administering a lipophilic platinum complex being dissolved or suspended in LPD, and then have accomplished the present invention.

That is, the summary of the present invention is as follows.

[1] A method for promoting the uptake of platinum complex into cancer cells, which comprising administering a solution or suspension of a lipophilic platinum complex in LPD.

[2] The method according to the above [1], wherein the cancer cells are cisplatin-resistant cancer cells.

[3] An agent for treatment of cisplatin-resistant cancer, which comprises as an active ingredient a lipophilic platinum complex being dissolved or suspended in LPD.

[4] The agent for treatment according to the above [3], wherein the cisplatin-resistant cancer is a cancer having a resistant mechanism by inhibiting the uptake of cisplatin.

[5] The agent for treatment according to the above [3] or [4], wherein the lipophilic platinum complex has (1R,2R)-1,2-diaminocyclohexane as a ligand.

[6] The agent for treatment according to the above [3] or [4], wherein the lipophilic platinum complex is a platinum complex of the following formula:

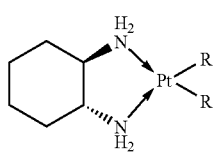

wherein R is a straight chain or branched chain $C_2$-$C_{24}$ saturated fatty acid residue which may optionally be substituted by one or more halogen atoms, or a straight chain or branched chain $C_8$-$C_{24}$ unsaturated fatty acid residue which may optionally be substituted by one or more halogen atoms.

[7] The agent for treatment according to the above [3] or [4], wherein the lipophilic platinum complex is SM-11355.

[8] The agent for treatment according to one of the above [3] to [7], wherein the cancer is a solid cancer.

[9] The agent for treatment according to one of the above [3] to [8], wherein the cancer is hepatic cancer, lung cancer or kidney cancer.

[10] The agent for treatment according to one of the above [3] to [9], which is formulated in a dosage of 10 to 200 mg/day.

EMBODIMENTS FOR CARRYING OUT THE INVENTION

Figure 1:
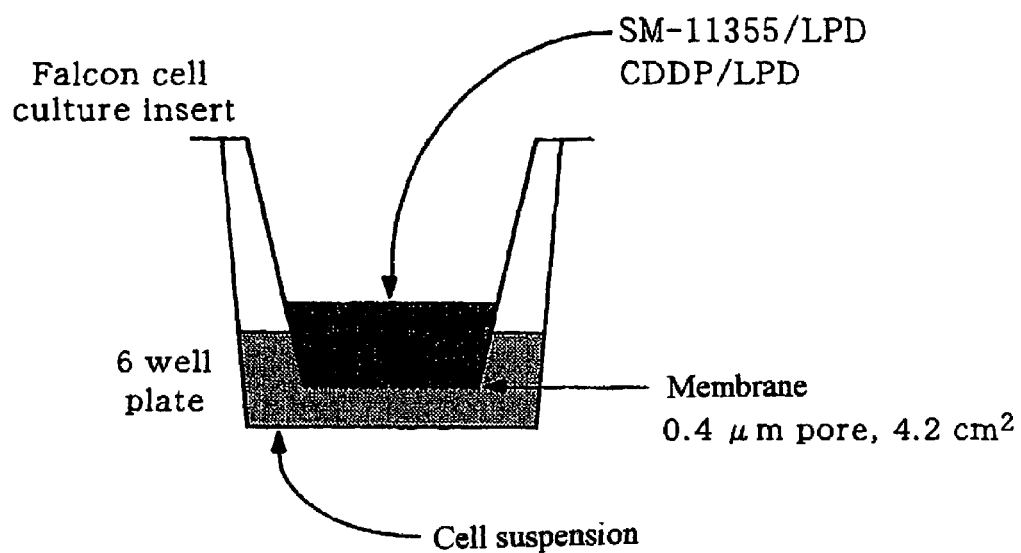
FIG. 1 is a schematic diagram illustrating the membrane method for evaluating the cell proliferation inhibitory effect of SM-11355/LPD and CDDP/LPD.

The "cisplatin-resistant cancer" includes either spontaneous resistant cancer or acquired resistant cancer. The spontaneous resistant cancer means a cancer which is congenitally hardly affected by the anti-tumor activity of cisplatin. The acquired resistant cancer means a cancer which initially shows sensitivity to cisplatin, but later posteriori acquires the resistance thereto after the continuous administration of cisplatin. There are usually mixed cancer cells of a cancer cell being high sensitive to cisplatin and a cancer cell being low sensitive to cisplatin even in one kind of cancer. In such a case, the high sensitive cancer cells often become extinct by contacting with cisplatin and change to the acquired resistant cancer cells. The agent for treatment of cisplatin-resistant cancer of the present invention is efficacious to both of the spontaneous resistant cancers and the acquired resistant cancers, but in preferred embodiment, the agent of the present invention is more efficacious to the acquired cisplatin-resistant cancers. Further, many of the cisplatin-resistant cancers show cross-resistance to the second generation platinum complexes such as Carboplatin (Cancer Research, 47, 414-418 (1987)), Iproplatin (ibid., 47, 414-418 (1987)), Nedaplatin (Jpn. J. Cancer Chemother., 23, 379-387 (1996)), etc. Therefore, in the present invention, the cisplatin-resistant cancer includes cancers showing resistance also to other platinum complexes as long as they show resistance to cisplatin.

The "lipophilic platinum complex" includes platinum complexes having a lipophilic base such as an amine, a diamine, pyridine, etc. as a ligand, specifically SM-11355 (JP-A-62-96, EP 193936), cis-bis(neodecanoato)-(1R,2R)-1,2-diaminocyclohexane platinum (II) (PCT/JP-A-63-501568, U.S. Pat. No. 5,041,581), Eptaplatin, Oxaliplatin (Biolchem. Pharmacol., 52, 1855-1865 (1996)), Lobaplatin (Pharmaceutical Research, 9, 808-811(1992)), Satraplatin (Cancer Chemotherapy & Pharmacology, 43 Suppl:S61-68(1999)), Cycloplatin (Zentralblatt für Gynakologie, 112, 1463-1467 (1990)), Ormaplatin (Cancer Research, 53, 799 (1993)), ZD 0473 (Journal of Inorganic Biochemistry, 77, 111-115 (1999)), JM 473 (European Journal of Cancer, 36, 1984-1990 (2000)). Preferred lipophilic platinum complex is a platinum complex having (1R,2R)-1,2-diaminocyclohexane as a ligand. More preferred platinum complex is a platinum complex of the formula:

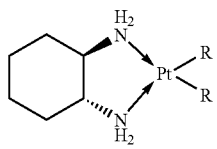

wherein R is as defined above, specifically includes SM-11355 and cis-bis(neodecanoato)-(1R,2R)-1,2-diaminocyclohexane platinum (II), etc. The pharmaceutically acceptable salts of those lipophilic platinum complexes and their solvates (e.g. hydrate) are also included in the present invention.

The "straight chain or branched chain $C_2$-$C_{24}$ saturated fatty acid residue" includes for example, residues of acetic acid, propanoic acid, butyric acid, pentanoic acid, pivalic acid, hexanoic acid, octanoic acid, 2,2-dimethyl-octanoic acid, capric acid, lauric acid, myristic acid, palmitic acid, stearic acid, arachidonic acid, behenic acid, lignoceric acid, etc., preferably $C_{10}$-$C_{24}$ saturated fatty acid residues, more preferably a residue of myristic acid, 2,2-dimethyloctanoic acid, etc. The "straight chain or branched chain $C_2$-$C_{24}$ saturated fatty acid residue which is substituted by a halogen atom" includes a straight chain or branched chain $C_2$-$C_{24}$ saturated fatty acid residue which is substituted by one or plural (e.g. 2 to 7) atoms of a chlorine atom, a bromine atom, or an iodine atom, specifically trifluoroacetic acid, pentafluoropropanoic acid, 5-chlorohexanoic acid, etc.

The "straight chain or branched chain $C_8$-$C_{24}$ unsaturated fatty acid residue" includes for example, residues of oleic acid, linoleic acid, etc., preferably straight chain or branched chain $C_{16}$-$C_{20}$ unsaturated fatty acid residues. The "straight chain or branched chain $C_8$-$C_{24}$ unsaturated fatty acid residue which is substituted by a halogen atom" includes a straight chain or branched chain $C_8$-$C_{24}$ unsaturated fatty acid residue which is substituted by one or plural (e.g. 2 to 7) atoms of a chlorine atom, a bromine atom, or an iodine atom.

The preparation of a lipophilic platinum complex being dissolved or suspended in LPD is usually used as an injection. For example, it can be administered into an artery to the cancer tissue, and in case for the treatment of hepatic cancer, it can be administered to the hepatic artery. For this treatment, the platinum complex is contained in a concentration of about 10 to 50 mg/ml in the solution or suspension. The preparation of the lipophilic platinum complex being dissolved or suspended in LPD may be prepared by dissolving or suspending the lipophilic platinum complex in LPD just before administration. For such a purpose, a lyophilized preparation (JP-A-3-255025) may be used as the lipophilic platinum complex.

The dose and number of administration times of the lipophilic platinum complex may vary depending on the symptoms, ages, body weights of the patients and the administration forms, but it is usually administered in a dose of about 1 mg to about 1000 mg per day, preferably about 5 mg to about 300 mg per day, more preferably about 10 to about 200 mg per day. It may repeatedly be administered at an interval of about one month to about 5 months, preferably about two months to about 3 months.

EXAMPLES

The present invention is illustrated by the following examples but should not be construed to be limited thereto.

Example 1

Anti-tumor Effects on CDDP-resistant Hepatic Cancer

1. Materials

An SM-11355 lyophilized product manufactured by Sumitomo Pharmaceuticals Company, Limited was used. CDDP was purchased from Wako Pure Chemical Industries, Ltd., and LPD was purchased from Mitsui Pharmaceutical Co., Ltd. WST-1 (2-(4-iodophenyl)-3-(4-nitrophenyl)-5-(2,4-disulfo-phenyl)-2H-tetrazolium, sodium salt) and 1-methoxy PMS (1-methoxy-5-methylphenazinium methylsulfate) were purchased from Wako Pure Chemical Industries, Ltd. MEM medium was a product of GIBCO. The fetal bovine serum (FBS) was a product of ICN BIOMEDICALS. Other reagents were commercially available ones having highest quality.

2. Apparatus and Materials for an Experiment

The 6 well microplate was the product of item number of Iwaki Glass 3810-006 and the 96 well microplate was of Iwaki Glass 3810-096. Cell culture insert was the product of item number of Falcon 3090. Tissue culture flask was the product of item number of Iwaki Glass 3100-025.

3. Preparation of Drugs

SM-11355/LPD was prepared by adding LPD to SM-11355 lyophilized product so as to be in a concentration of 20 mg/ml, and diluting with LPD to a concentration for testing. CDDP/LPD was prepared by pulverizing powdery CDDP in agate-made mortar, thereto adding gradually LPD to prepare a suspension in a concentration of 2 mg/ml, followed by diluting with LPD to a concentration for testing. WST-1 reagent was prepared by dissolving WST-1 (4.1 mg) in a 1-methoxy PMS solution (3.1 ml) (said solution being prepared by dissolving 1-methoxy PMS 7 mg in PBS 100 ml).

4. Cells

Rat hepatic cancer H4-II-E was obtained from Dainippon Pharmaceutical Co., Ltd. The H4-II-E cells were cultured in MEM medium, during which the concentration of CDDP was increased stepwise from 0.1 µg/ml to 1.0 µg/ml over a period of about one year, by which method, the CDDP resistant cell line (H4-II-E/CDDP) was prepared. The cells used in the experiment were those obtained by subculturing in a CDDP-containing MEM medium (CDDP 1.0 µg/ml) in vitro.

The cell proliferation inhibitory effects of cisplatin to H4-II-E cells and H4-II-E/CDDP cells after treating for 7 days were evaluated by WST-1 assay. As a result, H4-II-E/CDDP cells showed about 10-folds higher resistance to cisplatin in comparison with H4-II-E cells. H4-II-E/CDDP cells did not show any resistance to the anti-tumor drugs such as doxorubicin and etoposide which have an action mechanism different from that of platinum complex, and hence, said cells were not multiple drugs resistant cells. It was suggested that the mechanism exhibiting a resistance to cisplatin in H4-II-E/CDDP cells would largely be due to decrease of the amount of platinum within the cells.

5. Cell Proliferation Inhibitory Effects (Membrane Method)

The cell proliferation inhibitory effect of SM-11355/LPD was compared with the cell proliferation inhibitory effect of CDDP/LPD. Since when LPD preparation was directly added to the cell suspension, the cells were injured due to direct contact of the cells with LPD, it can not evaluate the cell proliferation inhibitory effect of the test drug per se. Accordingly, the LPD preparation was contacted to the cancer cells via a membrane, thereby only the test drug passed through the membrane were transferred into the cell suspension, and thereby the effect could be evaluated. In this viewpoint, the membrane method (as illustrated in FIG. 1) was newly constructed and used in the present experiment.

The H4-II-E cells or H4-II-E/CDDP cells were adjusted to $2.5 \times 10^3$ cells/ml and seeded to 6 well microplate in an amount of each 2 ml/well, and as a control (for Day 0) the cell suspension was seeded to 96 well microplate in an amount of each 100 µl/well and subjected to pre-culture for one day. To the plate in control was added WST-1 reagent in an amount of each 20 µl/well, and it was cultured in a $CO_2$ incubator for 2 to 3 hours. After culturing, the absorbance of the cell suspension (wavelength for measurement: 450 nm, wavelength for reference: 650 nm) was measured with Immuno Reader NJ-2001 (Inter Med).

A culture cell insert was put on each well of the 6 well microplate and thereto were added SM-11355/LPD or CDDP/LPD, LPD as a control, and the medium (2 ml), which were contacted with the cells via a membrane, and it was cultured in a $CO_2$ incubator for 7 days. After culturing, the cells were recovered and seeded on 96 well microplate in an amount of each 100 µl/well. Thereto was added WST-1 reagent in an amount of each 20 µl/well, and the cells were cultured in a $CO_2$ incubator for a predetermined period of time respectively, and thereafter the absorbance was measured. The T/C (%) was calculated by the following equation to obtain the $IC_{50}$ value.

$$T/C(\%) = \frac{\begin{bmatrix} \text{Absorbace of the cell suspension} \\ \text{teated with test drugs (Day 7)} \end{bmatrix} - \begin{bmatrix} \text{Absorance of the cell suspension} \\ \text{in control (Day 0)} \end{bmatrix}}{\begin{bmatrix} \text{Absorbace of the cell suspension} \\ \text{teated with } LPD \text{ alone (Day 7)} \end{bmatrix} - \begin{bmatrix} \text{Absorance of the cell suspension} \\ \text{in control (Day 0)} \end{bmatrix}} \times 100$$

Figure 2:
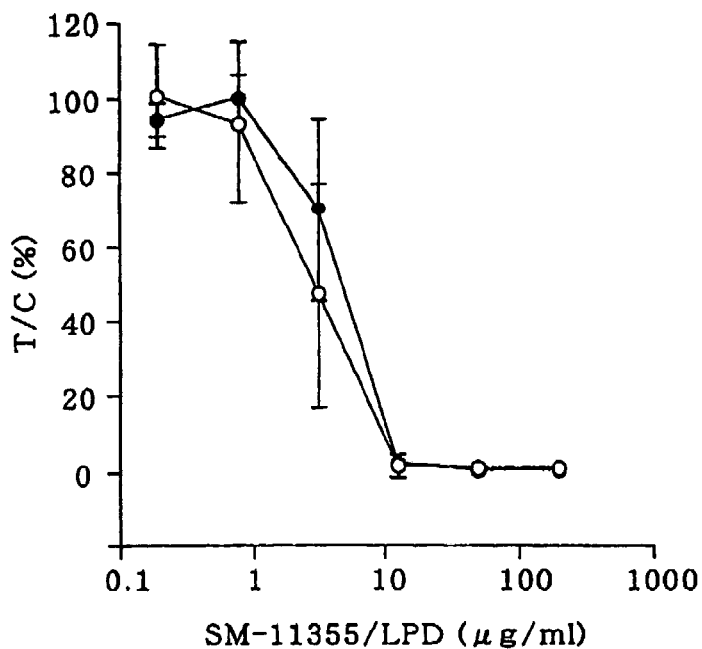
FIG. 2 is a drawing showing the cell proliferation inhibitory effect of SM-11355/LPD in membrane method against H4-II-E cells (○) and H4-II-E/CDDP cells (●). Plots in the drawing are the data (n=3-4) being expressed in mean±SD.
Figure 3:
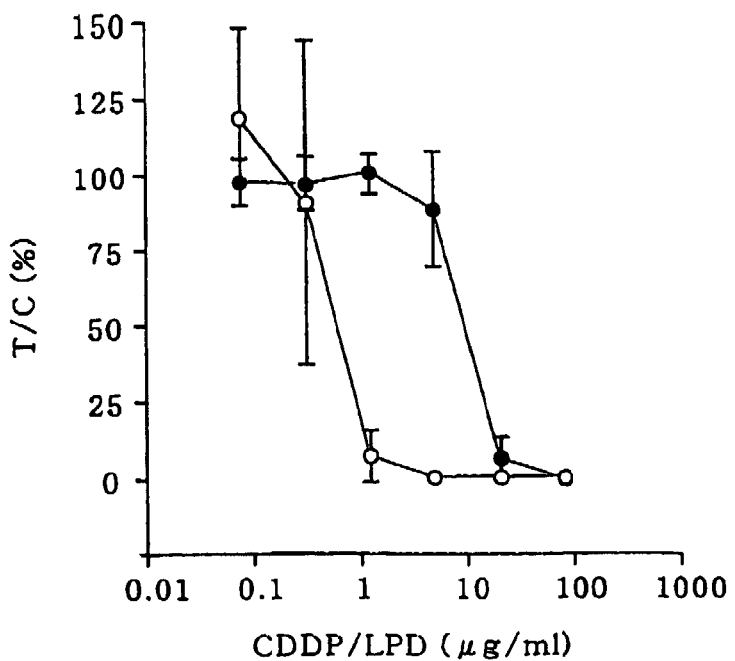
FIG. 3 is a drawing showing the cell proliferation inhibitory effect of CDDP/LPD in membrane method against H4-II-E cells (○) and H4-II-E/CDDP cells (●). The experiment was carried out by treating each cell with CDDP/LPD in various concentrations, and culturing for 7 days, and evaluating by WST-1 assay. The plots in the drawing are the data (n=3-4) being expressed in mean±SD.

The results are shown in FIG. 2 and FIG. 3. As is shown in FIG. 3, it was found that the $IC_{50}$ values of CDDP/LPD to H4-II-E cells and H4-II-E/CDDP cells were 0.57 µg/ml and 9.6 µg/ml, respectively, and there was about 20-folds difference between them. Besides, as is shown in FIG. 2, it was found that the $IC_{50}$ of SM-11355/LPD to both cells were 3.1 µg/ml and 4.6 µg/ml, respectively and the values in both cells were almost the same. Since SM-11355/LPD showed also cell proliferation inhibitory effect even to H4-II-E/CDDP cells, it was suggested that SM-11355/LPD could exhibit the effects without being affected by the mechanism of acquiring the resistance to CDDP in H4-II-E/CDDP cells.

Example 2

Uptake of Platinum into H4-II-E Cells and H4-II-E/CDDP Cells

The amount of uptake of platinum into H4-II-E cells and H4-II-E/CDDP cells was measured by membrane method for SM-11.355/LPD and CDDP/LPD.

The number of H4-II-E cells and H4-II-E/CDDP cells was adjusted to $4\times10^5$ cells/ml, and the cells were seeded onto 6 well microplate in an amount of each 2 ml/well, and subjected to pre-culture for one day. A cell culture insert was put on each well of the 6 well microplate and thereto were added SM-11355/LPD (50 μg/ml) and CDDP/LPD (80 μg/ml) in an amount of each 2 ml, which were contacted with the cells via a membrane, and those were cultured in a $CO_2$ incubator for 7 days as to SM-11355/LPD or for 3 days as to CDDP/LPD. After culturing, the cells were recovered, and the amount of platinum per $10^6$ cells was measured by an atomic-absorption spectroscopy (Z-9000, manufactured by Hitachi, Ltd.). The amount of platinum in cells is shown by mean±SD (n=3).

TABLE 1

| LPD preparation | Cells | Amount of platinum in cells (ng/$10^6$ cells) |
|---|---|---|
| CDDP/LPD | H4-II-E cells | 37.9 ± 30.2 |
| The same above | H4-II-E/CDDP cells | 8.1 ± 3.2 |
| SM-11355/LPD | H4-II-E cells | 86.1 ± 39.1 |
| The same above | H4-II-E/CDDP cells | 43.8 ± 11.2 |

Although the platinum complex was gradually released from SM-11355/LPD, it gave greater amount of uptake of platinum in H4-II-E cells and further greater amount of uptake of platinum in H4-II-E/CDDP cells in comparison with those in CDDP/LPD.

INDUSTRIAL APPLICABILITY

The present invention provides a method for promoting the uptake of a platinum complex into cancer cells by administering a solution or suspension of a lipophilic platinum complex in an iodized poppyseed oil fatty acid ethyl ester, and further provides an agent comprising as an active ingredient a lipophilic platinum complex dissolved or suspended in an iodized poppyseed oil fatty acid ethyl ester, which is useful for the treatment of cisplatin-resistant cancers.

The invention claimed is:

1. A method for treatment of cisplatin-resistant solid hepatic cancer, which comprises administering a solution or suspension of cis-[((1R,2R)-1,2-cyclohexane-diamine-N,N') bis (myristato)]platinum (II) of the formula:

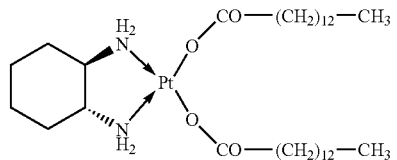

in an iodized poppyseed oil fatty acid ethyl ester to a subject having a cisplatin-resistant solid hepatic cancer.

2. The method for treatment according to claim 1, wherein the cisplatin-resistant solid hepatic cancer is a cancer having a resistant mechanism by inhibiting the uptake of cisplatin.

3. The method for treatment according to claim 1, wherein the cis [((1 R,2R)-1,2-cyclohexane-diamine-N,N') bis (myristato)]platinum (II) is formulated in a dosage of 10 to 200 mg/day.

4. The method for treatment according to claim 1, wherein the solution or of supension of the cis-[((1R,2R)-1,2-cyclohexane-diamine-N,N') bis(myristato)]platinum (II) is administered via an artery to the cancer tissue.

* * * * *